(12) United States Patent
Ahl

(10) Patent No.: US 12,383,175 B2
(45) Date of Patent: Aug. 12, 2025

(54) STICKPACK-TYPE PACKAGING FOR A TEST STRIP

(71) Applicant: Roche Diabetes Care, Inc., Indianapolis, IN (US)

(72) Inventor: Axel Ahl, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 18/399,924

(22) Filed: Dec. 29, 2023

(65) Prior Publication Data

US 2024/0130650 A1   Apr. 25, 2024
US 2024/0225500 A9   Jul. 11, 2024

Related U.S. Application Data

(62) Division of application No. 17/052,751, filed as application No. PCT/EP2019/061386 on May 3, 2019, now abandoned.

(30) Foreign Application Priority Data

May 4, 2018   (EP) .................................... 18170830

(51) Int. Cl.
*A61B 5/15*   (2006.01)
*A61B 5/145*   (2006.01)
(Continued)

(52) U.S. Cl.
CPC .... *A61B 5/150305* (2013.01); *A61B 5/14532* (2013.01); *A61B 5/150358* (2013.01);
(Continued)

(58) Field of Classification Search
CPC . A61B 5/150305; A61B 5/14532; B65B 9/20; B65B 61/002; B65B 61/025; B65D 75/12; B65D 75/44; B65D 75/5827
See application file for complete search history.

(56) References Cited

U.S. PATENT DOCUMENTS 3,642,450 A * 2/1972 Eriksson ............ B65D 75/5827
                                                      422/409
6,409,680 B1 * 6/2002 Caillouette .......... G01N 33/528
                                                      600/584
(Continued)

FOREIGN PATENT DOCUMENTS

CN       202414431       9/2012
CN       203037656       7/2013
(Continued)

OTHER PUBLICATIONS

AZO UTI test strips retrieved Dec. 12, 2024 from; https://azoproducts.com/products/azo-test-strips (Year: 2015).*
(Continued)

*Primary Examiner* — Jill A Warden
*Assistant Examiner* — Alex Ramirez
(74) *Attorney, Agent, or Firm* — Woodard, Emhardt, Henry, Reeves & Wagner, LLP

(57) ABSTRACT

The application concerns a stickpack-type packaging comprising an elongate foil tube having two transverse sealing joints, such that a tightly closed fill space is provided in the foil tube for storing a product. It is proposed that a single disposable test strip is arranged in the fill space, wherein the test strip has a chemistry pad for detecting an analyte in a sample, and the chemistry pad is arranged at a distance at least from one of the transverse sealing joints.

22 Claims, 2 Drawing Sheets

(51) Int. Cl.
*B65B 9/20* (2012.01)
*B65B 61/00* (2006.01)
*B65B 61/02* (2006.01)
*B65D 75/12* (2006.01)
*B65D 75/44* (2006.01)
*B65D 75/58* (2006.01)

(52) U.S. Cl.
CPC .............. *B65B 9/20* (2013.01); *B65B 61/002* (2013.01); *B65B 61/025* (2013.01); *B65D 75/12* (2013.01); *B65D 75/44* (2013.01); *B65D 75/5827* (2013.01)

(56) References Cited

U.S. PATENT DOCUMENTS

| | | | |
|---|---|---|---|
| 9,089,293 | B2 | 7/2015 | Haar et al. |
| 2004/0131805 | A1* | 7/2004 | Merical .................. A61B 50/30 |
| | | | 428/34.1 |
| 2011/0142377 | A1 | 6/2011 | Bradley |
| 2012/0012490 | A1* | 1/2012 | Brownell .............. B65B 43/465 |
| | | | 53/445 |
| 2013/0343968 | A1* | 12/2013 | Ootsuka .................... B01L 3/00 |
| | | | 422/555 |
| 2016/0310939 | A1* | 10/2016 | Titmus .................... B01L 3/505 |
| 2018/0003621 | A1 | 1/2018 | Drury |

FOREIGN PATENT DOCUMENTS

| | | |
|---|---|---|
| DE | 202012001106 | 3/2012 |
| EP | 1 464 587 | 10/2004 |
| EP | 2 749 882 | 7/2014 |
| GB | 1451268 | 9/1976 |
| JP | 1992031205 | 2/1992 |
| JP | 2004238010 | 8/2004 |
| JP | 2008024370 | 2/2008 |
| JP | 2009161252 | 7/2009 |
| JP | 2016078891 | 5/2016 |
| KR | 20140053274 | 5/2014 |
| RU | 2016125243 | 1/2018 |

OTHER PUBLICATIONS

International Search Report for PCT/EP2019/061386 mailed Jun. 5, 2019.

* cited by examiner

STICKPACK-TYPE PACKAGING FOR A TEST STRIP

The invention concerns a stickpack-type packaging comprising an elongate foil tube preferably having a longitudinal sealing joint, wherein two transverse sealing joints are provided on the longitudinal ends of said foil tube, such that an essentially air and moisture tight closed fill space is provided in the foil tube for storing a product. The invention further concerns a method for producing and a method for using such a stickpack-type packaging.

Among the various types of packaging for particulate products, a type denoted as "stickpack" is widely used commercially. Such stickpacks provide for several advantages, particularly from the perspective of continuous production and dosing of small product quantities.

In the field of blood glucose testing, it is known to use disposable test strips for measurements on the spot. The user provides a fresh blood sample by pricking a finger and transferring a drop of blood onto the test strip. For test strips to be optically evaluated, a chemistry pad is provided on a carrier for an enzymatic reaction to enable detection of the glucose concentration via a color change. These test strips are usually sold in larger quantities of e.g. 50 strips in a vial or test strip container.

On this basis an object of the invention is to further expand the production and application of stickpack-type packaging concepts and to provide enhanced user convenience and special product protection specifically in problematic environments.

The combination of features stated in the independent claims is proposed to achieve this object. Advantageous embodiments and further developments of the invention are derived from the dependent claims.

The invention is based on the idea of providing a single disposable test strip in a user-friendly packaging. Thus, a stickpack packaging is proposed in which a single disposable test strip is arranged in the fill space, wherein the test strip has a chemistry pad for detecting an analyte in a sample, and the chemistry pad is arranged at a distance at least from one of the transverse sealing joints. In this arrangement, it is largely avoided that reactive components in the chemistry pad are impaired by negative impacts, specifically heat influence, during sealing of the packaging. For this purpose, a full faced chemistry coating of the test strip should be avoided, and the chemistry pad should be provided in an end section or a middle section of the test strip distant from at least one or both of the transverse sealing joints. The stickpack provides a compact receptacle with improved protection against environmental influences and specifically moisture and dust in ambient air. Thus, safety of test results can be guaranteed even under harsh conditions. Moreover, the single test quantity allows the user to buy and/or hold available only a required number of tests for a given time, without the need for carrying an unnecessary large packing volume.

Advantageously, the chemistry pad is arranged close to a first transverse sealing joint and at a larger distance from a second transverse sealing joint, wherein the first transverse sealing joint is provided prior to the test strip in the foil tube, such that the first transverse sealing joint cannot affect in its vicinity the chemistry pad.

A further improvement in this direction is achieved when the test strip comprises a carrier of a generally rectangular shape and the chemistry pad is provided in one end section and/or in an intermediate section of the carrier.

In order to account for an optical test evaluation, the foil tube has an imprint of one or more, preferably two to six and most preferably three reference colors on its outer surface, wherein the reference colors are adapted for comparing a color change of the chemistry pad resulting from a reaction with the analyte in order to evaluate a test result.

For an optimized color definition, the reference colors each are provided by a spot color which is premixed before printing.

As a still further advantageous measure, the reference colors define a color-scale and/or a gray-scale for comparing the color change of the chemistry pad.

According to a preferred implementation, the imprint comprises two reference color scales of different size, wherein a reference color scale of small size is provided in a first zone of the foil tube and a reference color scale of comparably larger size is provided on a second zone of the foil tube preferably arranged opposite to the first zone. Both scales should display the same reference colors. Thus, different methods of test evaluation—e.g. visual or by an instrument—can be employed.

The foil tube may be formed from one of the following alternatives:
i) a flexible flat web having a longitudinal sealing joint joining its mutually opposite longitudinal edges,
ii) two pieces of a flexible flat web provided on top of each other and having two longitudinal sealing joints along their paired longitudinal edges,
iii) an extruded tube section which is free from longitudinal sealing joints.

Advantageously, the foil tube is formed from a composite-layer flat web preferably comprising an aluminum layer. This allows to provide a very flexible, tight and strong containment at low weight.

In order to additionally suppress influence of moisture, it can be further advantageous when the foil tube includes a desiccant for drying the fill space. The desiccant can be arranged inside the fill space or in a foil material of the foil tube.

A still further use improvement provides that the foil tube contains an adhesive area or a rubber lining on its outer surface for placing a used test strip thereon. It is also conceivable that a protective sheet is provided on the adhesive area on which the adhesive may partially adhere when it is detached, such that the sheet can be affixed elsewhere as a label, e.g. on a clinical report.

Another aspect of the invention concerns a method for producing a stickpack-type packaging comprising the steps of
a) forming an elongate foil tube preferably by joining mutually opposite longitudinal edges of a flexible flat web,
b) sealing the foil tube by first and second heat-sealed transverse joints provided on the longitudinal ends of the foil tube, thereby providing a tightly closed fill space for storing a product,
c) providing a disposable test strip having a chemistry pad for detecting an analyte in a sample,
d) introducing the test strip into the fill space before closing the second transverse sealing joint,
e) placing the test strip in step d) such that the chemistry pad is arranged at a distance from the second transverse sealing joint.

In this way, advantageous effects are achieved as outlined above in connection with the process product.

For further moisture reduction, it is advantageous to purge the fill space with dry gas and/or to dry the test strip before introducing it into the fill space.

As a further advantageous measure, an imprint of one or more reference colors is applied to the starting foil material such that the imprint appears on the outer surface of the foil tube.

Advantageously, the foil tube is formed by one of the following steps:
i) joining mutually opposite longitudinal edges of a flexible flat web preferably by a heat-sealed longitudinal joint;
ii) providing two congruent pieces of a flexible flat web on top of each other and joining their paired longitudinal edges by respective longitudinal sealing joints,
iii) cutting a section from an extruded tube material.

A still further aspect of the invention concerns a use of a stickpack-type packaging comprising the following steps:
a) providing a stickpack-type packaging including a single disposable test strip,
b) withdrawing the test strip from the packaging by tearing the foil tube preferably at a pre-weakened or saw-toothed tear section,
c) applying a sample, preferably of a body fluid to the chemistry pad,
d) comparing a color change of the chemistry pad resulting from a reaction with the analyte to the imprint of reference colors in order to evaluate a test result.

Advantageously, the comparison of the color is made optically by an instrument, in particular a mobile device preferably including a digital camera (specifically a smart phone), or visually by a user.

In the following, the invention is further elucidated on the basis of an embodiment example shown schematically in the drawings, where FIG. 1 shows a front view of stickpack packaging including a single disposable test strip;

Figure 1:
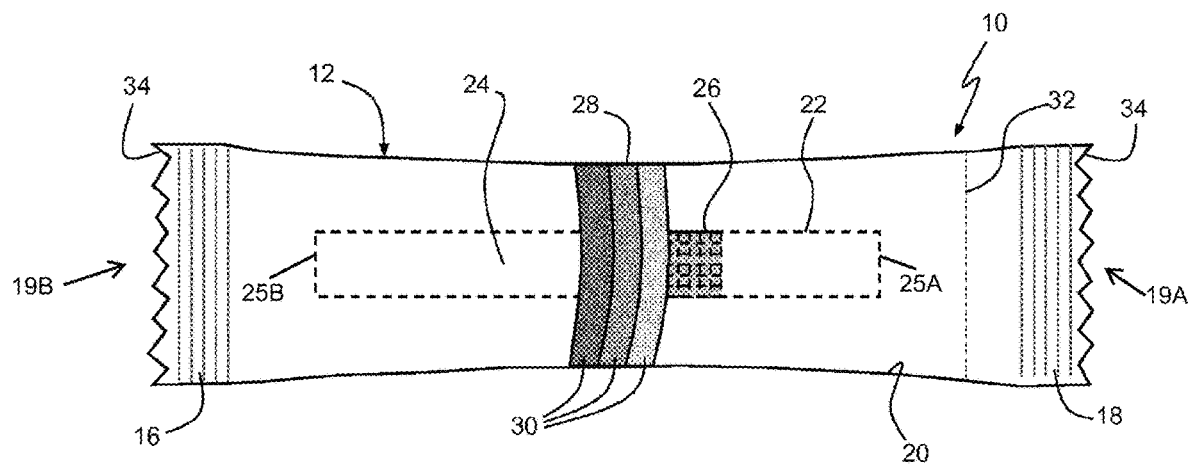
Figure 2:
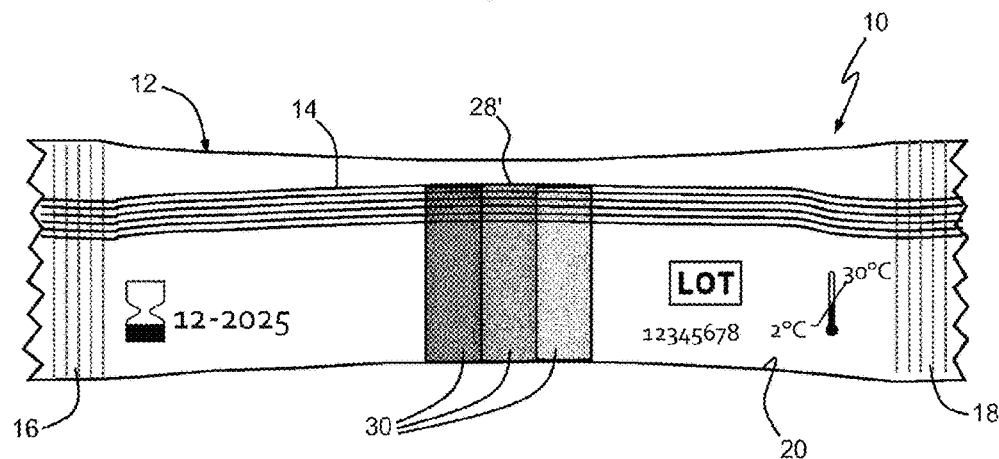
FIG. 2 is a back view of the stickpack of FIG. 1.
Figure 3:
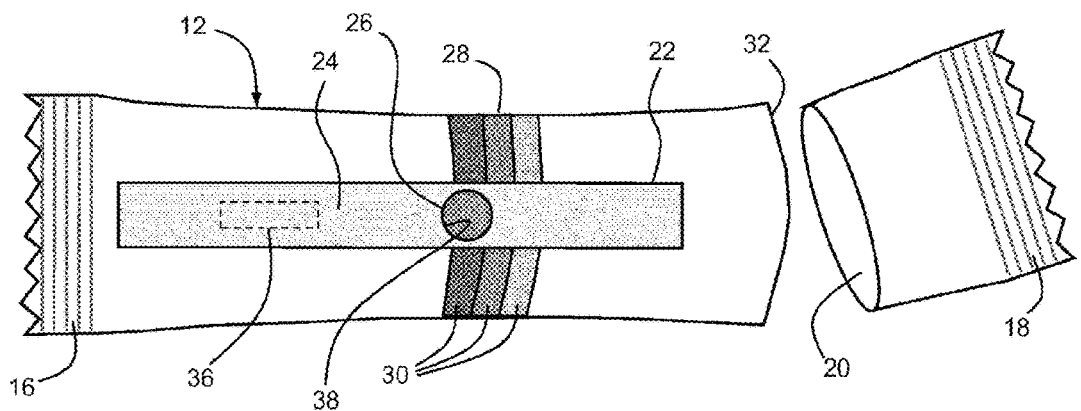
FIG. 3 shows the opened stickpack of FIG. 1 and the test strip attached to the outside.

As depicted in FIGS. 1 to 3, an exemplary embodiment of a stickpack packaging 10 comprises an elongate foil tube 12 closed by a longitudinal sealing joint 14 and two transverse sealing joints 16, 18 at the first longitudinal end 19A and the second longitudinal end 19B, respectively, of the foil tube 12, such that a fill space 20 is closed on all sides, wherein a single disposable test strip 22 is arranged.

FIG. 1 shows the test strip 22 in phantom lines enclosed in the fill space 20. The test strip 22 has a rectangular carrier foil 24 and a heat sensitive chemistry pad 26 in a section of the carrier foil 24. The heat sensitive strip 22 comprises a dosing end 25A and a meter end 25B. The chemistry pad 26 contains enzymes and auxiliary substances like mediators for detecting an analyte in a liquid sample, specifically for glucose in a blood sample. Such test strips 22 are known per se and are available e.g. under the trade name ACCU-Chek. It is also conceivable that the test strips are intended for other purposes, e.g. for measuring lactate or cholesterol level.

The chemistry pad 26 is susceptible to heat, moisture and other influences. While the foil tube 12 is essentially air and moisture tightly closed to shield against environmental influences during storage, measures should be taken to avoid thermal damage of the chemistry pad 26 during manufacturing of the package 10, as explained in more detail below.

The foil tube 12 has first and second imprints 28, 28' of a number of different reference colors 30 on its front and back side, respectively. The reference colors 30 define a color-scale and/or gray-scale for comparing a color change of the chemistry pad 26 resulting from a reaction with the analyte in order to evaluate a test result on the spot in order to guarantee fastness of colors, purposively spot colors are used which are premixed before the imprints 28, 28' are made on the starting material of the foil tube 12.

As shown in FIG. 1, a generally smaller imprint 28 on the front side is intended for an optical comparison carried out by an instrument. Such an instrument may be constructed as a mobile device including a digital camera, specifically a smart phone in conjunction with a diagnostic software application. Due to the reduced size of the imprint 28, an extended area of the front side may be used for manufacturer's labels or other information. FIG. 2 shows a comparatively larger imprint 28' on the back side, which can for a device-independent visual color comparison conducted by the user. Each of the imprints 28, 28' may contain three reference colors 30, representing low, medium and high analyte concentration.

An end section of the foil tube 12 may be provided with a pre-weakening tear line 32 running transverse to the longitudinal tube axis. Another option for simplified tearing the packaging 12 open in longitudinal direction may be provided by tooth-shaped transversal edges 34.

As illustrated in FIG. 3, the test strip 22 may be used by tearing the tear line 32, applying the blood sample to the chemistry pad 26 of the withdrawn test strip 22 and comparing the color change, caused by reaction of the chemistry pad 26 with the analyte, to the imprint 28. The last step can be carried out by attaching the upper side of the test strip 22 to an adhesive area 36 on the foil tube 12 such that the arrangement remains fixed during capture of an image by a camera. In this way, the color of the test field 26 can be evaluated from the rear side through a hole 38 in the carrier 24 and instrumentally compared to the imprint 28.

Prior to use, the adhesive area 36 may be covered by a detachable label or sheet (not shown), on which the adhesive may partially adhere when it is detached from the foil tube 12, such that the label can be affixed elsewhere, e.g. on a clinical report.

Figure 4:
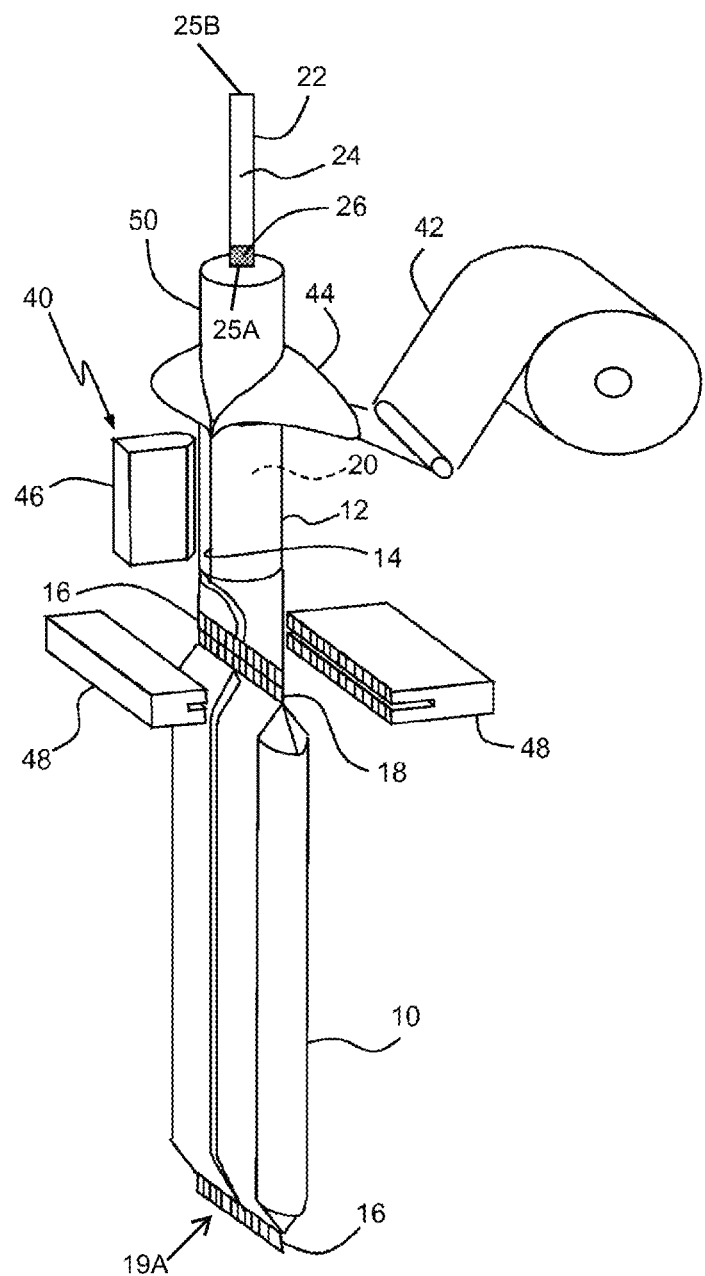
FIG. 4 is a schematic view of a machine for manufacturing of a stickpack including a test strip.

FIG. 4 illustrates the production of the packaging 10 in a continuous vertical mode of operation in a stickpack machine 40. As a starting material, a flat web 42 is unwound from a roll and formed into a tube on a forming shoulder 44. The starting material 42 consists of a composite-layer material including an aluminum layer and an inner sealing layer and is already provided with the imprints 28, 28' prior to forming the tube 12.

The inner sealing layer may consist of a thermoplastic polymer, namely Polyethylene (PE) or Polypropylene (PP) or a copolymer of both or a combination with other plastic materials. Thus, mutually opposed sealing layers can be fusion bonded under the influence of heat and pressure over a given time. Advantageously, these parameters may be adjusted in the range of sealing temperatures from 110 to 200° C., sealing pressures of 0.5 to 5 bar and sealing times of 0.3 to 2 s. In this connection, the influence of the sealing temperatures and times on the chemistry pad 26 should be taken into account.

Accordingly, mutually opposite longitudinal edges of the tubular foil body are heat-sealed by a vertical heat shoe 46 used to form the longitudinal sealing joint 14 before introducing a test strip 22.

The forming of the transverse sealing joints 16, 18 is achieved pairwise by engaging horizontal heat shoes 48, which also include a corrugated knife for cutting the edges 34. In this way, the upper transverse sealing joint 18 of a preceding packaging 10 is provided at the same time as the lower transverse sealing joint 20 of a trailing foil tube 12.

A vertical supply tube 46 extends into the fill space 20 and allows to introduce a test strip 22 carrying the chemistry pad 26. For keeping the fill space 20 free of moisture, it is conceivable to purge the fill space with dry gas and/or drying the test strip 22 in advance. Another option is providing the starting material 42 with a desiccant.

As mentioned above, the chemistry pad 26 should not be thermally stressed by the heat shoes 46, 48. This can be achieved by suitable arrangement and feeding of the test strip 22, such that the chemistry pad 26 is arranged at a distance from at least one of the transverse sealing joints 16, 18.

In the configuration shown in FIG. 4, the longitudinal sealing joint 14 and the lower transverse sealing joint 16 are formed prior to introducing the test strip 22. After removing the heat shoes 46, 48, the chemistry pad 26 can be placed headfirst on the lower end section of the carrier 24, such that it has the maximum distance to the impact of heat during closing of the upper transverse sealing joint 18 in the following phase. Of course, it is also conceivable that the chemistry pad 26 is arranged in a middle section of the carrier 24, as shown in FIG. 1, whereas a full faced chemistry coating or an arrangement of the chemistry pad 26 in the upper end section without remaining distance to the closing transverse sealing joint 18 should be avoided.

The invention claimed is:

1. A method for producing a stickpack-type packaging containing a test strip having a first end and a second end, a heat sensitive chemistry pad being located adjacent the first end, comprising:
   a) forming an elongate foil tube having a first longitudinal end and a second longitudinal end;
   b) sealing the first longitudinal end of the elongate foil tube by a first heat-sealed transverse joint, thereby providing an open fill space for receiving the test strip;
   c) after step b), introducing the test strip into the open fill space with the first end being inserted first and being received adjacent the first longitudinal end; and
   d) after step c), sealing the second longitudinal end of the elongate foil tube by a second heat-sealed transverse joint, thereby closing the open fill space containing the test strip,
   wherein the heat sensitive chemistry pad is arranged in the packaging closer to the first heat-sealed transverse joint than to the second heat-sealed transverse joint.

2. The method of claim 1 in which the heat sensitive chemistry pad is located in a middle section of the test strip.

3. A method for producing a stickpack-type packaging containing a test strip, the method comprising:
   a) forming an elongate foil tube having a first longitudinal end and a second longitudinal end;
   b) sealing the first longitudinal end of the foil tube by a first heat-sealed transverse joint, thereby providing an open fill space for receiving the test strip;
   c) after step b), introducing the test strip into the open fill space; and
   d) after step c), sealing the second longitudinal end of the elongate foil tube by a second heat-sealed transverse joint, thereby closing the open fill space containing the test strip,
   wherein the test strip has a first end and a second end, the test strip having a heat sensitive chemistry pad for detecting an analyte in a sample, the heat sensitive chemistry pad being closer to the first end than to the second end, the first end of the test strip being introduced into the open fill space first, the heat sensitive chemistry pad being located in the fill space closer to the first longitudinal end than to the second longitudinal end.

4. The method according to claim 3 wherein the heat sensitive chemistry pad is arranged closer to the first heat-sealed transverse joint than to the second heat-sealed transverse joint.

5. The method of claim 3, and further comprising purging the open fill space with dry gas before introducing the test strip into the open fill space.

6. The method of claim 3, and further comprising drying the test strip before introducing it into the open fill space.

7. The method of claim 6, and further comprising purging the open fill space with dry gas before introducing the test strip into the open fill space.

8. The method according to claim 3, wherein step a) comprises forming the elongate foil tube by a method selected from the group consisting of:
   i) joining opposed longitudinal edges of a flexible flat web;
   ii) providing two congruent pieces of a flexible flat web on top of each other and joining their paired longitudinal edges by respective longitudinal sealing joints, and
   iii) cutting a section from an extruded tube material.

9. The method of claim 8 wherein forming the elongate foil tube comprises joining opposed longitudinal edges of a flexible flat web.

10. The method of claim 9 in which joining the opposed longitudinal edges comprises joining the edges by a heat-sealed longitudinal joint.

11. The method according to claim 3, wherein the foil tube is provided with an adhesive area or a rubber lining on its outer surface for placing a used test strip thereon.

12. The method of claim 3 wherein step (b) comprises tearing the foil tube at a pre-weakened or tooth-shaped tear section.

13. A method for using a stickpack-type packaging comprising:
   a) providing a stickpack-type packaging obtained by the method according to claim 3;
   b) withdrawing the test strip from the packaging by tearing the foil tube;
   c) applying a sample to the chemistry pad; and
   d) comparing a color of the chemistry pad resulting from a reaction with the analyte to one or more reference colors in order to evaluate a test result.

14. The method of claim 13 comprising the elongate foil tube having an outer surface comprising an imprint of the one or more reference colors, wherein the comparison of the color is made optically by a mobile device including a digital camera.

15. The method of claim 14 wherein step c) comprises applying a body fluid to the chemistry pad.

16. A method for packaging a test strip, the method comprising:
   a) forming an elongate foil tube having a first longitudinal end and a second longitudinal end;
   b) sealing the first longitudinal end of the foil tube by a first heat-sealed transverse joint, thereby providing an open fill space for receiving the test strip;

c) after step b), introducing the test strip into the open fill space, the test strip having a first end and a second end, the test strip comprising a heat sensitive chemistry pad located on the test strip closer to the first end than to the second end, the test strip being introduced into the open fill space with the first end being inserted first and being positioned in the fill space with the first end being closer to the first longitudinal end than to the second longitudinal end; and d) after step c), sealing the second longitudinal end of the elongate foil tube by a second heat-sealed transverse joint, thereby closing the open fill space containing the test strip.

17. The method of claim 16 in which the heat sensitive chemistry pad is located adjacent to the first end of the test strip.

18. The method of claim 16 in which the heat sensitive chemistry pad is located in a middle section of the test strip.

19. The method of claim 16 in which forming of the second heat-sealed transverse joint is accomplished under conditions which could cause damage to the heat sensitive chemistry pad if the first end of the test strip was not inserted first.

20. The method of claim 16 in which forming of the second heat-sealed transverse joint is accomplished at a temperature of 110° to 200° C.

21. A method for packaging a test strip, the method comprising:

a) forming an elongate foil tube having a first longitudinal end and a second longitudinal end;

b) sealing the first longitudinal end of the foil tube by a first heat-sealed transverse joint, thereby providing an open fill space for receiving the test strip;

c) after step b), introducing the test strip into the open fill space, the test strip being arranged in the fill space with the heat sensitive chemistry pad a distance from the second longitudinal end to prevent damage upon sealing the second longitudinal end; and d) after step c), sealing the second longitudinal end of the elongate foil tube by a second heat-sealed transverse joint, thereby closing the open fill space containing the test strip.

22. The method of claim 21 in which the heat sensitive chemistry pad is located in a middle section of the test strip.

* * * * *